US00PP31203P2

(12) United States Plant Patent
Olesen et al.

(10) Patent No.: US PP31,203 P2
(45) Date of Patent: Dec. 10, 2019

(54) ***CLEMATIS* PLANT NAMED 'EVIPO080'**

(50) Latin Name: *Clematis viticella*
Varietal Denomination: Evipo080

(71) Applicants: Mogens Nyegaard Olesen, Fredensborg (DK); Raymond J. Evison, St Sampsons Vale (GB)

(72) Inventors: Mogens Nyegaard Olesen, Fredensborg (DK); Raymond J. Evison, St Sampsons Vale (GB)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,904

(22) Filed: Sep. 10, 2018

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./228
CPC ..... A01H 5/02; A01H 5/00
See application file for complete search history.

(56) References Cited

PUBLICATIONS https://www.rhs.org.uk/plants/pdfs/plant-register-supplements/Clematis/6th-Clematis-Supplement.pdf; 2018; 1 page.*

* cited by examiner

*Primary Examiner* — Kent L Bell

(57) ABSTRACT

A new *Clematis* plant with a compact growth habit, profuse, violet purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo080'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2003 and the resulting seeds were planted the following winter in a controlled environment in Guernsey, Channel Islands, United Kingdom. The new variety named 'Evipo080' originated as a single seedling from the stated cross.

The new *Clematis* plant may be distinguished from its female seed parent and male pollen parent by the following characteristics. The female seed parent has red purple tepals while the new variety has violet purple tepals. The male seed parent has red purple tepals, while the new has violet purple tepals.

The objective of the hybridization of this *Clematis* plant was to create a new and distinct variety for nursery culture with unique qualities such as:

1. Uniform and abundant violet purple flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo080' was selected by Mogens N. Olesen and Raymond J. Evison in their *Clematis* development program in the Channel Islands, United Kingdom in 2004. Asexual reproduction of 'Evipo080' by means of vegetative cuttings and traditional layering was first performed by Mogens N. Olesen and Raymond J. Evison in the nursery during the summer of 2004. This initial and subsequent asexual propagations have demonstrated that the characteristics of 'Evipo080' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo080'.

Specifically illustrated in FIG. 1 of the drawings is an open flower, tepals detached, a flower bud, and a flowering stem.

DETAILED DESCRIPTION OF THE VARIETY

Figure 1:
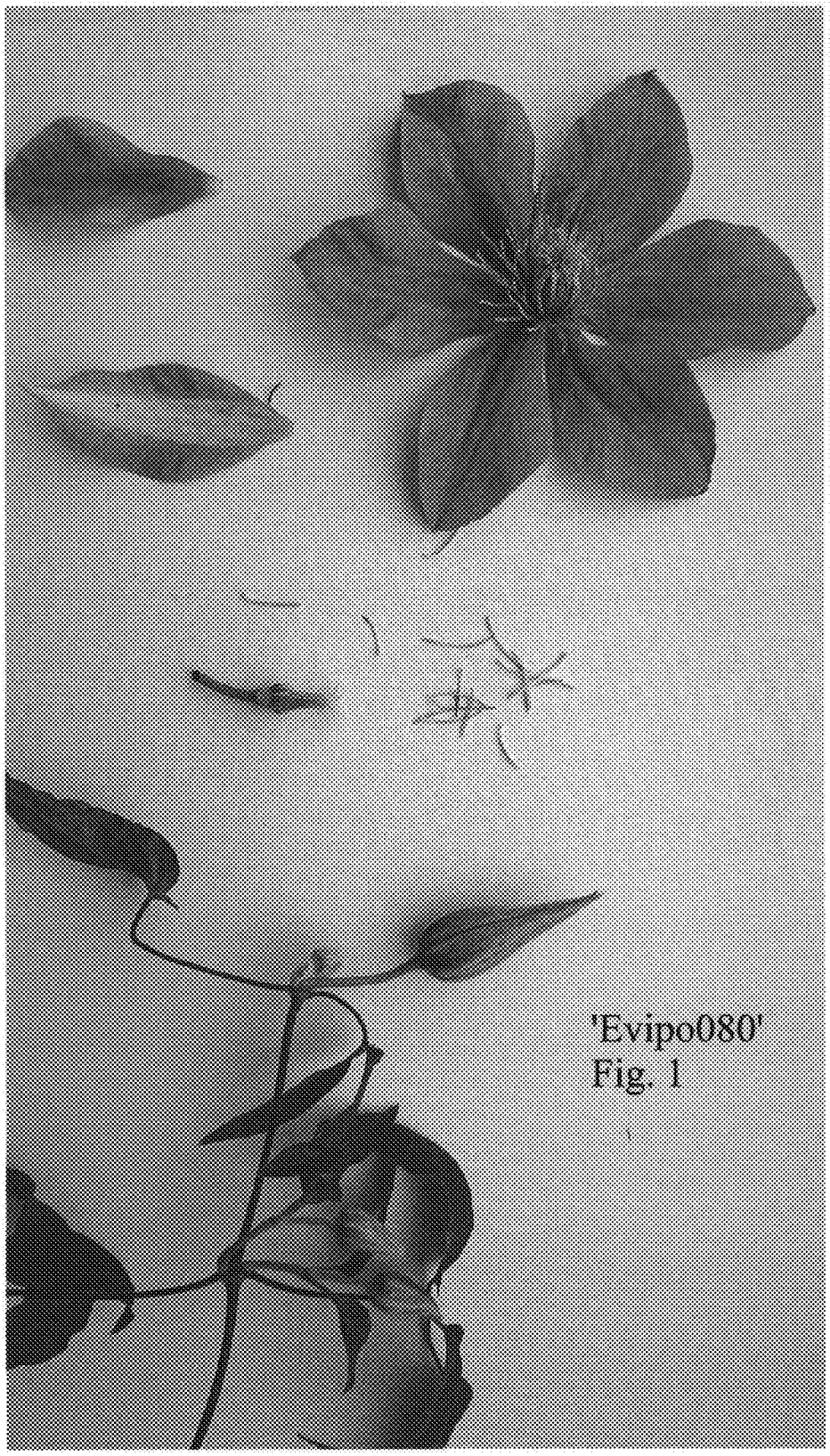
Figure 2:
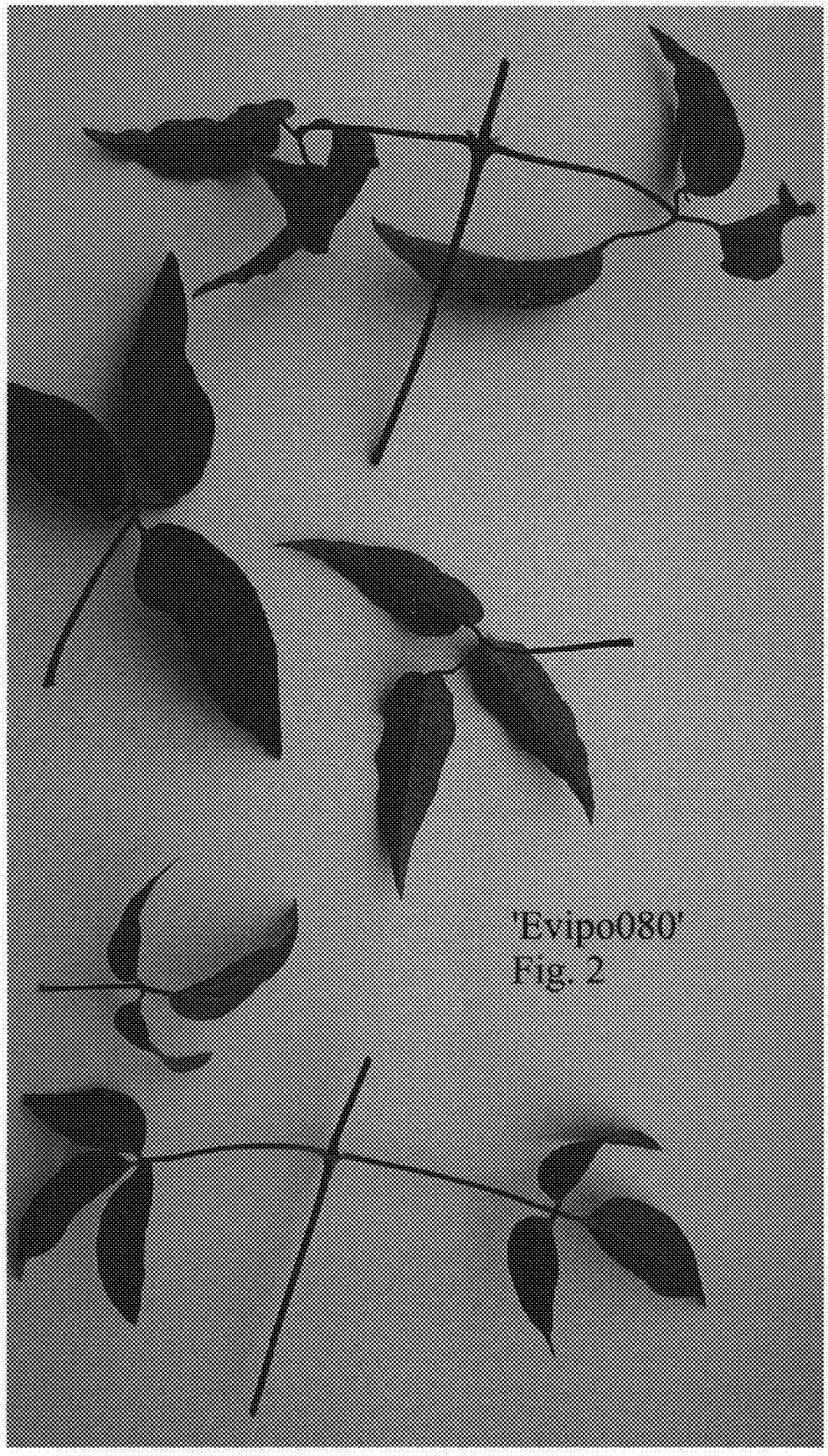
FIG. 2 shows leaves and stems. Illustrated plants are 2 years of age.

The following is a detailed description of 'Evipo080', as observed in its growth throughout the flowering period in Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo027' described and illustrated in U.S. Plant Pat. No. 27,281 are compared to 'Evipo080' in Chart 1.

CHART 1

| | 'Evipo080' | 'Evipo027' |
|---|---|---|
| Flower diameter | 100 mm | 145 mm |
| Tepal upper surface | Violet Group 88D with intonations of Red-Purple Group N74A and a stripe of Purple-Violet Group 82B | Red-Purple Group 70 B with a central bar which is a blend of Red-Purple Group 71A and 71B |
| Tepal count | 6 | 6 to 8 |

FLOWER AND FLOWER BUD

Blooming habit: Continuous. The natural flowering period is generally from April to September.

Flower bud:
- *Size.*—Normally 35 mm in length. Bud diameter is 12 mm.
- *Bud form.*—Elliptic.
- *Bud color.*—Yellow-Green Group 145A and Violet 88D.
- *Texture.*—Pubescent.

Pedicel:
- *Surface texture.*—Smooth and lightly pubescent.
- *Length.*—25 to 30 mm in length with 2 mm diameter.
- *Color.*—Yellow-Green Group 145A.
- *Strength.*—Moderately strong.

Receptacle:
- *Surface texture.*—Lightly pubescent.
- *Shape.*—Broad funnel.
- *Size.*—1 mm (h)×3 mm (w).
- *Color.*—Yellow-Green Group 145A.

Flower arrangement:
- *Location on vine.*—New growth only.
- *Borne.*—Singly, in each leaf axillary.

Flower bloom:
- *Size.*—Flowers are about 100 mm in diameter and 20 mm in depth.
- *Profile.*—Open flowers are flat.
- *Fragrance.*—None.
- *Lasting quality.*—Flowers normally remain up to 10 days on the plant.

Tepals:
- *Tepal color.*—The upper surface is Violet Group 88D with intonations of Red-Purple Group N74A and a stripe of Purple-Violet Group 82B. The lower surface is Violet Group 84B with a stripe of Green-White Group 157A.
- *Quantity.*—Normally 6 tepals.
- *Size.*—45 mm in length by 20-28 mm wide.
- *Shape.*—Individual tepal shape is elliptic. The tepal apex is acuminate. The tepal base is typically acute.
- *Apex recurvature.*—Slightly recurved.
- *Tepal cross section.*—Slightly reflexed or cupped.
- *Margins.*—Entire.
- *Persistence.*—Tepals drop off cleanly.
- *Tepal overlap.*—None.

Reproductive organs:
- *Pollen.*—None observed.
- *Anthers.*—Size: 5 mm in length. Color: Green Yellow 1 B. Quantity: On average, 70.
- *Filaments.*—Color: Green Yellow 1C. Length: 16 mm.
- *Pistils.*—Quantity: On average, 40.
- *Stigmas.*—Superior in location relative to the length of the filaments and the height of the anthers.
- *Styles.*—Color: Green White 157A. Length: 16 mm.

Seed head characteristics: Seed not observed to date.

PLANT

Plant form: Climbing.

Plant growth: Compact.

Size: In one season, the plant grows to 60 cm in height. Average spread is 50 cm.

Stems:
- *Color.*—Juvenile stems are Brown Group 200C. Mature stems are Greyed-Orange Group 166A.
- *Internodes.*—On average, 7 cm between nodes.
- *Length.*—Normally 30 cm from the base of the plant to the flowering portion of the stem.
- *Diameter.*—About 2 mm.
- *Texture.*—Mature stems are slightly ribbed.

Plant foliage:
- *Leaf characteristics.*—Deciduous.
- *Arrangement.*—Ternate.
- *Leaf size.*—Compound leaves are about 110 mm (l)× 120 mm (w). Leaflets are about 55 mm (l)×20 mm (w).
- *Abundance.*—On average 1 leaf per 10 cm of stem.
- *Leaf color.*—Juvenile upper Green Group 137C. Juvenile lower Green Group 138B. Mature upper Yellow-Green Group 147A. Mature lower Yellow-Green Group 147B.
- *Stipules.*—Absent.
- *Petioles.*—Size: Normally 35 to 45 mm in length by 1 mm diameter. Texture: Smooth, and lightly pubescent. Color: Brown Group 200C.
- *Petioloule.*—Size: 5 to 15 mm in length by 1 mm diameter. Texture: Smooth, and lightly pubescent. Color: Brown Group 200C.
- *Leaflet shape.*—Generally elliptic. The base is rounded, or oblique. The apex is acute.
- *Margin.*—Entire.
- *Surface.*—The upper side is smooth, the lower side is smooth.
- *Thickness.*—Moderate.
- *Glossiness.*—Moderately glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo080', substantially as described and illustrated, due to its abundant violet purple flowers with good keepability, attractive long lasting foliage and compact growth, suitability for production from softwood cuttings in pots, durable flowers and foliage which make the variety suitable for distribution in the floral industry.

* * * * *

'Evipo080'

'Evipo080'